United States Patent [19]

Hasegawa et al.

[11] Patent Number: 5,798,467
[45] Date of Patent: Aug. 25, 1998

[54] PLUCK RESISTANCE MEASURING INSTRUMENT FOR SNAP MEMBERS

[75] Inventors: Kenji Hasegawa; Katsushi Kitano. both of Tokyo, Japan

[73] Assignee: Scovill Japan Kabushiki Kaisha. Tokyo, Japan

[21] Appl. No.: 691,346

[22] Filed: Aug. 2, 1996

[30] Foreign Application Priority Data

Aug. 3, 1995 [JP] Japan ................. 7-216503

[51] Int. Cl.$^6$ ................. G01L 5/00
[52] U.S. Cl. ................. 73/862.01; 73/830; 73/856
[58] Field of Search ................. 73/760, 862.381, 73/856, 830, 862.01, 862.03, 851, 862.393

[56] References Cited

U.S. PATENT DOCUMENTS

| | | | |
|---|---|---|---|
| 3,718,039 | 2/1973 | Bacon et al. | 73/862.01 X |
| 3,830,101 | 8/1974 | Frey | 73/862.02 |
| 4,535,636 | 8/1985 | Blackburn et al. | 73/856 X |
| 4,753,115 | 6/1988 | Moody. | |
| 4,773,276 | 9/1988 | Baruffalo | 73/862.01 |
| 5,211,061 | 5/1993 | Goodwin | 73/862.01 X |

FOREIGN PATENT DOCUMENTS

| | | |
|---|---|---|
| 0186358 | 7/1986 | European Pat. Off. . |
| 0620183 | 3/1949 | United Kingdom . |
| 1379649 | 1/1975 | United Kingdom . |
| 2107476 | 4/1983 | United Kingdom . |

*Primary Examiner*—Elizabeth L. Dougherty
*Attorney, Agent, or Firm*—Sprung Kramer Schaefer & Briscoe

[57] ABSTRACT

An instrument for measuring the pluck resistance of snap-members has a presser for pressing the fabric of a garment to which a snap member is attached, securely around the member and a plurality of jaws for constraining the sides of the snap member. A tensile force pulls the snap member away in the direction at right angles to the fabric surface to which the snap member is attached and a gauge measures the tensile force.

10 Claims, 6 Drawing Sheets

PLUCK RESISTANCE MEASURING INSTRUMENT FOR SNAP MEMBERS

BACKGROUND OF THE INVENTION

This invention relates to an instrument for measuring the resistance of the snap members of snap fasteners to plucking from the fabrics of garments and the like to which they are attached.

Snap fasteners each consisting of a female snap member known as a socket and a male snap member known as a stud (the members being hereinafter called "snap members") are in abundant use on garments and the like. With those snap members the garment manufacturers are being required to assure certain pluck resistance as the Product Liability (PL) Act and regulations on small-size articles have come in force in the U.S. The snap fastener has a structure in which the male and female snap members are resiliently engaged or disengaged, the members being attached opposite to each other to mate on overlapping edges of a garment fabric. Each snap member is secured in place with a backing member known as a prong which consists of a flanged or annular base formed with several slender protrusions or prongs extending upright from the base. If the snap member thus secured to the fabric comes off easily, an infant can swallow it or the backing member. To avoid this danger, each snap member must be guaranteed to resist plucking with forces beyond a predetermined level.

Inspection for pluck resistance, therefore, has become necessary at sewing factories. It is quite likely that, since the PL Law has been enforced in Japan too, testing of this character will soon be imperative. At the present the manufacturers are determining the pluck resistance by their own testing procedures, because the enforcement regulations do not stipulate the measuring method. Consequently, the results vary so widely that they fail to furnish a proper, common basis for qualitative evaluation.

As described above, none of the conventional methods of measuring the pluck resistance of snap members are dependable at the present. Much variation of the measured values presents a problem of impossibility of proper evaluation.

The present invention is aimed at providing an instrument capable of measuring the pluck resistance of snap members accurately and promptly.

SUMMARY OF THE INVENTION

The present inventors have intensively studied about the method whereby the pluck resistance of snap members can be measured with less variation than heretofore for proper evaluation of the property. It has now been found that the following approach permits the most appropriate and reproducible (with little scatter) measurement, that is:

(1) pressing the fabric of a garment to which a snap member (socket or stud member) of a snap fastener has been attached with a prong or other similar backing member, securely around the snap member;

(2) while about the same time constraining the snap member with forces exerted in the directions at right angles to the sides of the member; and (3) pulling the snap member away in the direction at right angles to the surface of the fabric to which it is attached.

To realize this sequence of steps, the present invention provides a pluck-resistance measuring instrument for snap members which comprises means for pressing the fabric of a garment to which a snap member is attached, securely around the member, means for constraining the sides of the snap member, tensile means for pulling the snap member away in the direction at right angles to the fabric surface to which the member is attached, and means for measuring the tensile force exerted by the tensile means.

BRIEF DESCRIPTION OF THE DRAWINGS

FIG. 6 is a diagrammatic view of different snap members and backing members.

DETAILED DESCRIPTION OF THE INVENTION

Since the measurement of pluck resistance involves destruction, it does not directly indicate the pluck resistance of the individual garments to which the test snap members are attached. However, the measurement guarantees the pluck resistance of the snap members made of the same material and by the same manufacturing steps. In the form of a nondestructive test, a snap member may be pulled with a given tensile force. If the member does not come off, then it is a concrete guarantee for the pluck resistance to plucking forces up to that limit. It is therefore obvious that the measuring instrument is capable of performing both types of tests, destructive and nondestructive, and it should be taken for granted that the pluck resistance measurement according to this invention covers the both.

To be more exact, a fabric to which a snap member has been attached is placed on a table (stage), and a substantially horizontally extending, fabric presser arm is turned pivotally round a horizontal shaft to press the fabric around the snap member, preferably with an annular front end of the arm. As the means for pivotally moving the arm, one comprising a link connected at one end to the rear end of the arm, a link holder pivotally connected to the other end of the link, an arm-adjusting dial for slidably supporting the link holder, and a fixed, externally threaded shaft in thread engagement with an internally threaded center hole of the arm-adjusting dial may be used. The arm-adjusting dial may be turned by hand or motor-driven.

The means for constraining the sides of a snap member must be such that will not allow the constrained snap member to be set free while being pulled. To preclude the possibility, it has been found useful that the constraining means comprise a plurality of jaws having front ends horizontally engageable with the sides of the snap member, horizontal pivots supporting the individual jaws, and means for acting on the rear ends of the jaws to move the same pivotally round the horizontal pivots, the front ends of the jaws horizontally engageable with the sides of the snap member preferably having engaging faces substantially vertical with respect to the corresponding faces of the snap member.

The means for acting on the rear ends of the jaws to move the same pivotally round the horizontal pivots comprises a jaw-adjusting dial having a tapered surface which acts on the inner sides at the rear ends of the jaws and a fixed, externally threaded vertical shaft in thread engagement with an internally threaded center hole of the jaw-adjusting dial. Here again the jaw-adjusting dial may be turned manually or by an electric motor.

An embodiment of the present invention will be described in detail below with reference to the accompanying drawings. The embodiment is intended to illustrate the invention and is not to be construed to limit the scope of the invention.

Figure 1:
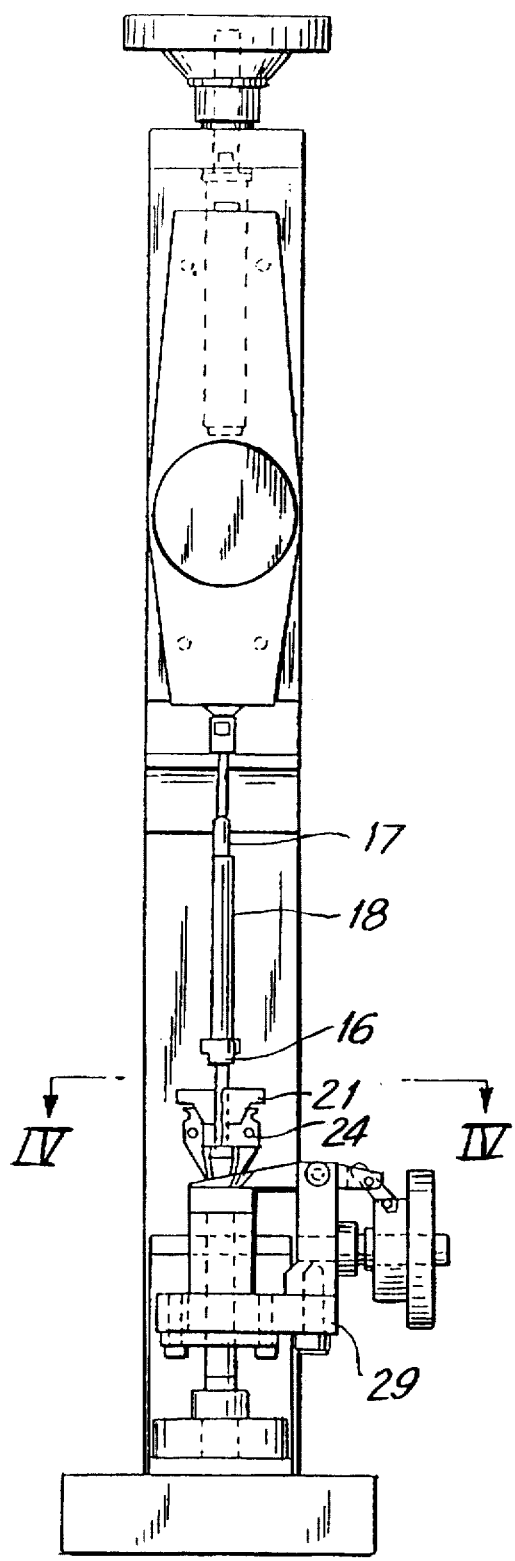
FIG. 1 is a front elevational view of a pluck-resistance measuring instrument embodying the present invention.
Figure 2:
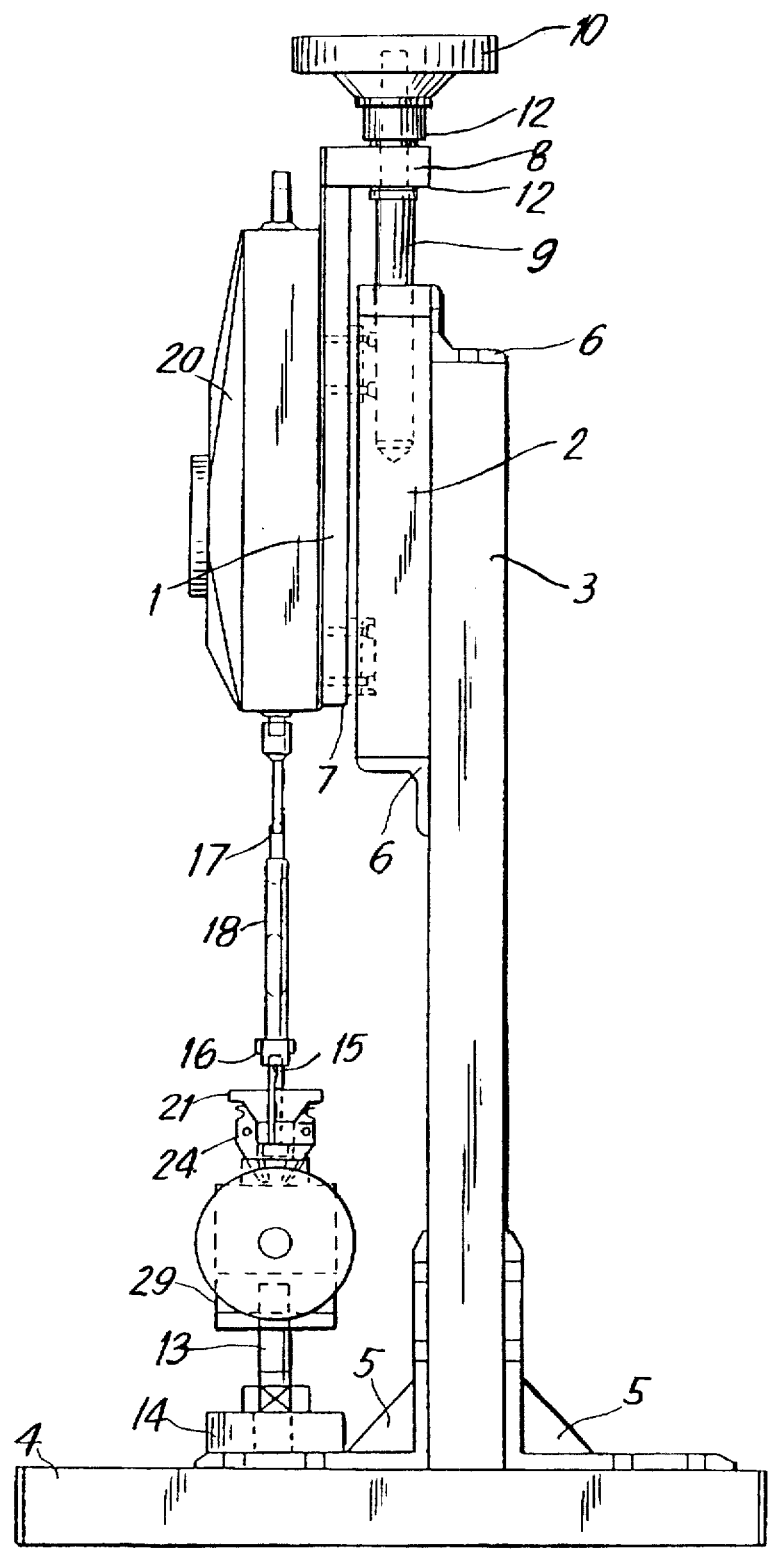
FIG. 2 is a right side elevational view of the instrument of the invention.

FIGS. 1 and 2 are general front and side elevational views, respectively, of a preferred embodiment of the pluck resistance measuring instrument of the invention.

An upright frame 3 is fixed to a base frame 4 with brackets 5, 5, and a support frame 2 is secured to the upper part of the upright frame with brackets 6, 6. The front side of the support frame is formed with a vertical dovetail groove, in which slide members 7 having a cross sectional contour complementary to the groove are received. The slide members 7 jointly carry a gage holder plate 1. The members thus far described are made of a metal, e.g., aluminum. A tensile force measuring gage 20 is supported by the gage holder plate 1. A top plate 8 is fixed to the upper end of the gage holder plate 1. The top plate 8 is formed with a vertical hole, through which extends the upper end portion of an externally threaded vertical bolt 9 whose lower end portion is in thread engagement with an internally threaded vertical hole of the support frame 2. The threaded bolt shank 9 has a large-diameter section (lead shank) in contact with the upper and under surfaces of the top plate 8 through plastic washers 12, 12, so that the top plate 8 follows the vertical motion of the threaded bolt 9. A plastic wheel 10 is fixedly mounted on top of the threaded bolt 9 and is caused to turn manually or electrically.

The construction is such that, as the wheel 10 is turned, the threaded bolt 9 turns too, with consequent upward or downward movement of the lead shank, and hence of the gage holder plate 1 and the tensile force measuring gage 20.

A commercially available tension gage may be used as the gage 20. From the lower end of the tension gage 20 extends a chain 17 sheathed in a resin tube 18 and terminating with a joint 16. The underside of the joint has a vertical blind hole threaded internally, into which the upper end portion of an externally threaded vertical bolt 15 is screwed. The threaded bolt 15 carries at its lower end a set of jaws 24 and a jaw-adjusting dial 21 which altogether constitute tensile means to be detailed later.

A support mount 14 is fixed to the upper surface of the base frame 4, and a support bolt 13 stands upright from the support mount 14. The upper end of the support bolt 13 is in thread engagement with an internally threaded hole of a support block 29. The support block 29 supports a fabric-supporting stage of a testing table and means for pressing a fabric in position, both of which are to be described in detail below.

The details of the testing table and tensile means will now be described in conjunction with FIGS. 3 to 5.

Figure 3:
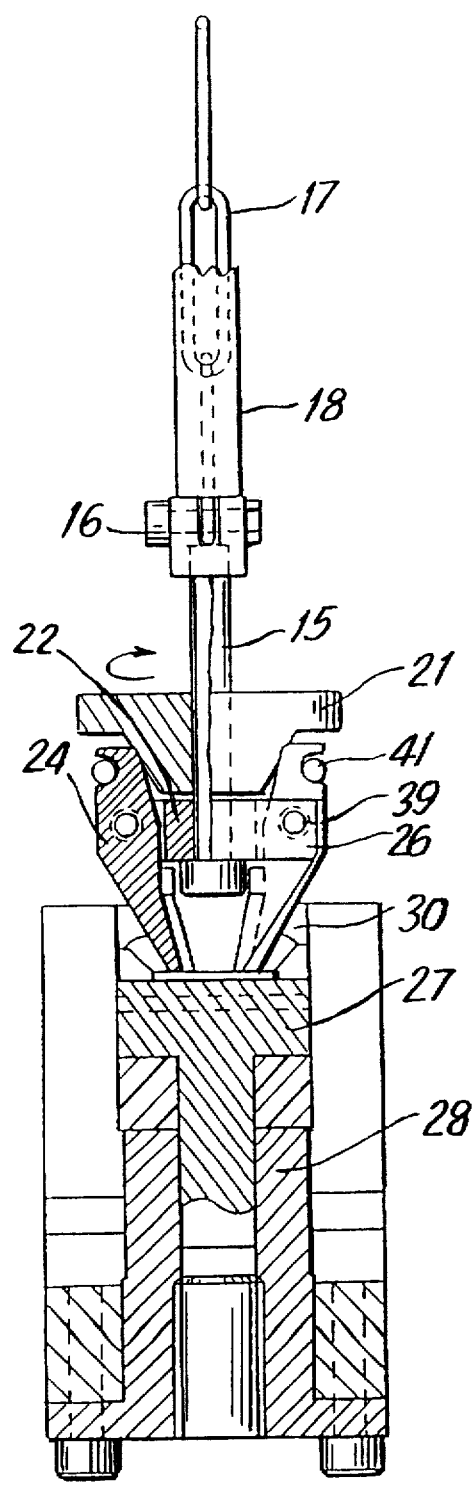
FIG. 3 is a partial enlarged front view, partly in section, of the instrument of the invention.

FIG. 3 is an enlarged view, partly in section, of a frontal portion of FIG. 1. FIG. 4 is a plan view taken on the line IV—IV of FIG. 1, and FIG. 5 is a sectional view taken on the line V—V of FIG. 4. A vertical cylindrical member 28 is fixedly mounted on the support block 29 with setscrews. A columnar leg 19 of a die 27 having a flat top surface to support a fabric and snap members is inserted into the vertical bore of the vertical cylindrical member 28 through a flexible ring, e.g., of polyurethane rubber. This arrangement prevents the fabric presser means from exerting excessive pressure.

A presser arm 30 having an annular front end to press the fabric portion around a snap member extends over the top surface of the die 27. The arm 30 is supported by a horizontal shaft 38, which in turn rests on an arm-supporting block 35 fixed integrally to the support block 29 with a bolt. To the rear end of the presser arm 30 is connected the front end of a link 33 with a pin 34. The rear end of the link 33 is connected to a generally disk-shaped link holder 32. The link holder 32 has a groove to engage with the rear end of the link 33 and is constrained from turning, but it is movable along its central axis. The link holder 32 is supported, through a bearing 42, on a sleeve of an arm-adjusting dial 31 that is internally threaded and meshed with the external thread of a threaded horizontal shaft 36 fixed to the arm-supporting block 35. The numeral 45 designates a retaining washer for the link holder 32, 43 designates a thrust bearing for the dial 31, and 44, 44 are retaining washers.

Figure 4:
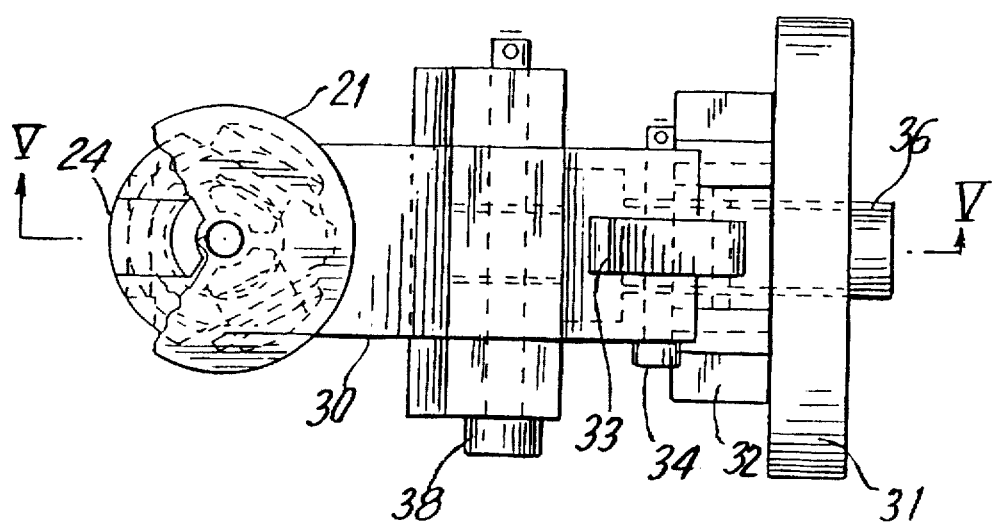
FIG. 4 is a plan view taken on the line IV—IV of FIG. 1.
Figure 5:
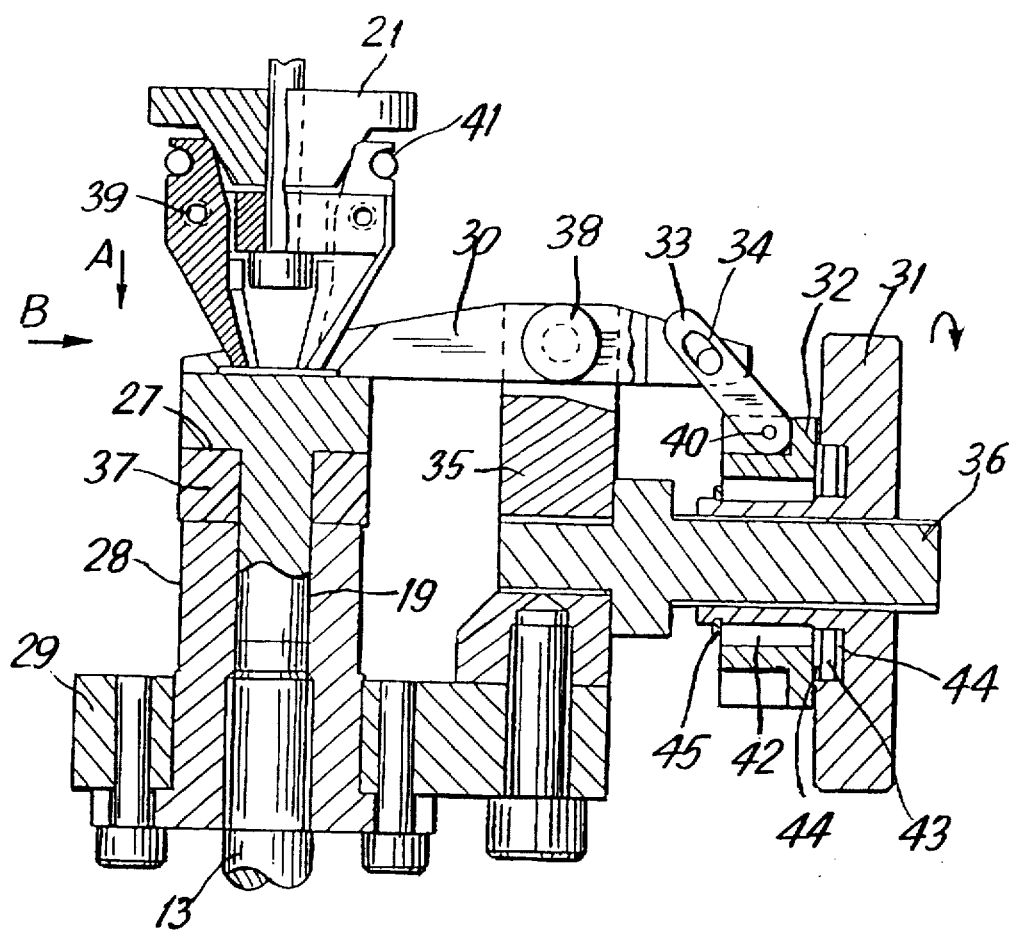
FIG. 5 is a sectional view taken on the line V—V of FIG. 4.

Turning the dial 31 clockwise moves it leftward as viewed in FIGS. 4 and 5, forcing the link holder 32 in the same direction, thereby urging the link 33 leftward. Thus the fabric presser arm 30 can turn counterclockwise pivotally around the horizontal shaft 38 to press the fabric with a snap member located in the space of its annular front end. This dial may be designed to turn manually or automatically.

Next, the means for retaining the side faces of a snap member will be explained. Referring to FIGS. 3 to 5, the threaded bolt 15 is in thread engagement with the joint 16 connected to the lower end of the chain extending downward from the tensile force measuring gage 20, as already described. The threaded bolt 15 has a large-diameter head formed at the lower end, which supports a horizontal jaw-supporting plate 26. A plurality of jaws 24, three being shown, are attached to the jaw-supporting plate 26 with horizontal pivots 39. As better shown in FIG. 7, the jaws 24 are tapered at the lower end, with the inner side 46 being nearly vertical. The inner side 46 need not be exactly vertical but if it inclines too far from the vertical axis, a snap member cannot be gripped securely, leading to an error in measurement. The jaws 24 have a peripheral groove each formed along the outer periphery, and a ring of coiled spring 41 is fitted in those grooves of the jaws 24 to bias the lower ends of the jaws normally in the open position. Above the jaws, the threaded bolt 15 extends through, in thread engagement with, an internally threaded hole of the jaw-adjusting dial 21, so that a truncated conical lower part of the bolt projecting downward can push apart the upper inner side portions of the jaws 24. Here again the jaw-adjusting dial 21 may be designed to turn manually or automatically.

With the construction described, turning the jaw-adjusting dial 21 clockwise on its vertical axis moves the jaws 24 pivotally around the horizontal pivots 39 to grip a snap member by its sides.

Figures 6A, 6B, 6C, 6D, 7:
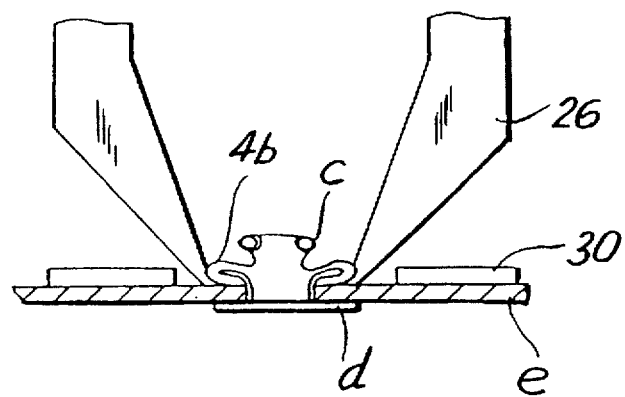
FIG. 7 is a diagrammatic view of a snap member attached to one side of a fabric.

As will be appreciated on the whole from the above explanation, the operation of the pluck-resistance measuring instrument for snap members will be described in detail below. FIG. 6 illustrate various examples of snap members to be tested In the drawing, (a) and (d) are backing members of the same structure, each having prongs for securing a snap member in place. (b) is a male snap member having an enlarged flange. (c) is a female snap member likewise having an enlarged flange. For testing, the test pieces are held securely, as shown in FIG. 7, between the inner sides at the lower ends of the jaws 24.

As FIG. 7 shows, e.g., a female snap member (c) is attached to a fabric (e) with a backing member (d), and they are altogether placed on the die 27 at a point where the female snap member (c) is aligned with the axis of the threaded bolt 15. Next, the jaw-adjusting dial 21 is turned to hold the snap member rigid on sides in a constrained position, and also the presser arm-adjusting dial 31 is worked to press the fabric in place with the annular front end of the presser arm 30. Then, the wheel 10 is turned to raise the tensile force measuring gage 20 slowly, and the gage reading is taken. If the snap member is not plucked off with the pull beyond a preset value, it means that the member has the preset pluck resistance. If the pulling is continued until the snap member comes off, the ultimate pluck resistance of the member is actually measured.

As will be clearly understood from the foregoing description, conventional methods of measuring the pluck resistance of snap members are not dependable at the present, and much variation of the measured values have hampered proper evaluation. The instrument according to the present invention can measure the pluck resistance of snap members accurately and promptly.

What is claimed is:

1. A pluck-resistance measuring instrument for snap members which comprises means for pressing the fabric of a garment to which a snap member is attached, securely around the member, a plurality of jaws for constraining the sides of the snap member, tensile means for pulling the snap member away in the direction at right angles to the fabric surface to which the member is attached, and means for measuring the tensile force exerted by the tensile means, wherein the fabric presser means comprises a fabric presser arm, a horizontal shaft supporting the arm, and means for acting on the rear end of the arm to move the rear end pivotally round the horizontal shaft.

2. The instrument of claim 1, wherein the means for acting on the rear end of the arm to move the same pivotally round the horizontal shaft comprises a link connected at one end to the rear end of the arm, a link holder pivotally connected to the other end of the link, an arm-adjusting dial for slidably supporting the link holder, and a fixed, externally threaded shaft in thread engagement with an internally threaded center hole of the arm-adjusting dial.

3. The instrument of claim 1 or 2, wherein the plurality of jaws have front ends horizontally engageable with the lateral sides of the snap member, horizontal pivots supporting the individual jaws, and means for acting on the rear ends of the jaws to move the rear ends of the jaws pivotally round the horizontal pivots.

4. The instrument of claim 3, wherein the front ends of the jaws horizontally engageable with the sides of the snap member have engaging faces substantially vertical with respect to the corresponding faces of the snap member.

5. The instrument of claim 3, wherein the means for acting on the rear ends of the jaws to move the rear ends of the jaws pivotally round the horizontal pivots comprises a jaw-adjusting dial having a tapered surface which acts on the inner sides at the rear ends of the jaws and a fixed, externally threaded vertical shaft in thread engagement with an internally threaded center hole of the jaw-adjusting dial.

6. A pluck-resistance measuring instrument for snap members, comprising: a support holding a fabric mounted snap member and for pressing down the fabric around the snap member; a plurality of jaws for engaging sides of the snap member; a member attached to the plurality of jaws for applying tensile force to the jaws and thereby to the snap member relative to the fabric to pull the snap member from the fabric; and a gauge for measuring the tensile force applied to the snap member, wherein the support comprises a presser arm for holding down the fabric around the snap member.

7. The instrument according to claim 6, further comprising a pivotally mounted arm support for the presser arm for moving the presser arm into a fabric holding position in response to the pivoting thereof.

8. The instrument according to claim 7, further comprising a rotatable dial and a linkage connecting the dial to the arm support to pivot the arm support in response to the rotation of the dial.

9. A pluck-resistance measuring instrument for snap members, comprising: a support holding a fabric mounted snap member and for pressing down the fabric around the snap member; a plurality of jaws for engaging sides of the snap member; a member attached to the plurality of jaws for applying tensile force to the jaws and thereby to the snap member relative to the fabric to pull the snap member from the fabric; and a gauge for measuring the tensile force applied to the snap member, wherein the jaws are pivotally mounted.

10. The instrument according to claim 9, further comprising a rotatable dial for pivoting the jaws to engage the snap member.

* * * * *